United States Patent [19]

Cooke

[11] Patent Number: 4,977,093

[45] Date of Patent: Dec. 11, 1990

[54] PROCESS FOR ANALYZING CARBONYL SULFIDE IN A GAS

[75] Inventor: Steven J. Cooke, Clarendon Hills, Ill.

[73] Assignee: Liquid Air Corporation, Walnut Creek, Calif.

[21] Appl. No.: 224,711

[22] PCT Filed: Nov. 3, 1986

[86] PCT No.: PCT/US86/02402

§ 371 Date: Apr. 7, 1988

§ 102(e) Date: Apr. 7, 1988

[51] Int. Cl.$^5$ .................... G01N 21/78; G01N 31/22
[52] U.S. Cl. ................... 436/119; 436/120; 436/121; 436/128; 436/175
[58] Field of Search ............ 436/127, 128, 119, 120, 436/121, 164, 167, 169, 175, 904; 422/83, 86, 88, 91; 423/437, 564, 244 R

[56] References Cited

U.S. PATENT DOCUMENTS

| | | | |
|---|---|---|---|
| 2,174,349 | 9/1939 | Littlefield | 436/121 |
| 3,300,282 | 1/1967 | Risk et al. | 436/121 |
| 3,607,073 | 9/1971 | Stamm | 436/140 |
| 3,725,009 | 4/1973 | Lovelock | 436/153 |
| 3,756,781 | 9/1973 | Kimbell | 436/123 |
| 3,853,474 | 12/1974 | Austin | 436/123 |
| 4,120,659 | 10/1978 | Cropper | 436/123 |
| 4,238,198 | 12/1980 | Swaim et al. | 436/123 |
| 4,332,781 | 6/1982 | Leider et al. | 423/226 |
| 4,352,779 | 10/1982 | Parks | 422/52 |
| 4,359,450 | 11/1982 | Blytas et al. | 423/564 |
| 4,472,977 | 11/1983 | Fisch | 423/226 |

OTHER PUBLICATIONS

Tilk, "The Determining of Organic Sulfur in Gases by the Catalytic Hydrolysis Method" Proc. of 42nd Annual Mtg. of Amer. Soc. for Testing Materials, 1939, vol. 39, pp. 1159-1170

Primary Examiner—Karen M. Hastings
Assistant Examiner—Laura Miles
Attorney, Agent, or Firm—George F. Bethel; Patience K. Bethel

[57] ABSTRACT

A process for the detection of carbonyl sulfide in a gas such as carbon dioxide is provided. The process comprises providing a known volume of gas to be analyzed and removing any hydrogen sulfide from the gas as by passage through a lead acetate column. The carbonyl sulfide is then converted to hydrogen sulfide. Preferably, this is accomplished by passage of the gas through acidified water and subsequent reaction by contact with an alumina hydrolysis catalyst. The converted $H_2S$ is then detected and measured. The amount of hydrogen sulfide detected represents an equimolar amount of carbonyl sulfide present in the original volume of gas. A portable, lightweight analyzer embodies the process and comprises a device for providing a known volume of gas to be analyzed; a device for removing hydrogen sulfide from the gas; a chemical for converting the carbonyl sulfide in the gas volume to hydrogen sulfide; a device for detecting and measuring the hydrogen sulfide in the gas; and conduits for connecting the above together.

16 Claims, 1 Drawing Sheet

PROCESS FOR ANALYZING CARBONYL SULFIDE IN A GAS

BACKGROUND OF THE INVENTION

1. Field of the Invention

This patent is directed to the field of detection of trace impurities in gases and particularly to a portable analyzer and process for the detection of carbonyl sulfide present in low part-per-million and part-per-billion concentrations in gases such as carbon dioxide gas.

2. Description of the Prior Art

Carbon dioxide gas is extensively used in the soft drink as well as the beer industries. Even very small amounts of carbonyl sulfide while odorless itself produces off-flavors in the food products in which the carbon dioxide contaminated with carbonyl sulfide is used. It is very difficult to detect low part-per-million (PPM) and part-per-billion (PPB) concentrations of carbonyl sulfide (COS) in gases such as carbon dioxide ($CO_2$).

It is desirable in the beverage industry to have an extremely accurate carbonyl sulfide analyzer which is inexpensive, portable, and extremely accurate to the extent of detecting carbonyl sulfide in carbon dioxide of less than 1 PPM.

One method for detecting carbonyl sulfide in gases is by means of a color tube produced by Bendix. This tube is based on an acid-base system which converts the carbonyl sulfide to sulfuric acid. The presence of carbonyl sulfide is indicated by a color change. The sensitivity of this test is not very good since the smallest amount of carbonyl sulfide which can be detected is 10 PPM. Moreover, it is not suitable for the detection of carbonyl sulfide in carbon dioxide because the carbon dioxide also reacts in the color tube.

Another means for detection of carbonyl sulfide is the use of a flame photometric detector (FPD). This device attaches to a gas chromatograph and is very accurate. The main drawbacks are that it is extremely costly, large in size, and requires a source of hydrogen and air as a fuel and nitrogen as a carrier gas.

SUMMARY OF THE INVENTION

The present invention provides a portable, lightweight analyzer to detect carbonyl sulfide in a gas which is light in weight and relatively low in cost when compared with prior art devices. Furthermore, it is extremely accurate to the extent of detecting carbonyl sulfide in carbon dioxide in concentrations as low as 0.05 PPM (50 PPB).

A process for the detection of carbonyl sulfide in a gas such as carbon dioxide is also provided. The process comprises providing a known volume of gas to be analyzed and removing any hydrogen sulfide from the gas. The carbonyl sulfide is then converted to hydrogen sulfide which is then detected and measured. The amount of hydrogen sulfide detected represents an equimolar amount of carbonyl sulfide present in the original volume of gas.

The portable, lightweight analyzer of the invention comprises means for providing a known volume of gas to be analyzed: means for removing hydrogen sulfide from the gas: means for converting the carbonyl sulfide in the gas volume to hydrogen sulfide: means for detecting and measuring the hydrogen sulfide in the gas: and conduit means for connecting the means together.

DETAILED DESCRIPTION OF THE INVENTION

The Process

Figure 1:
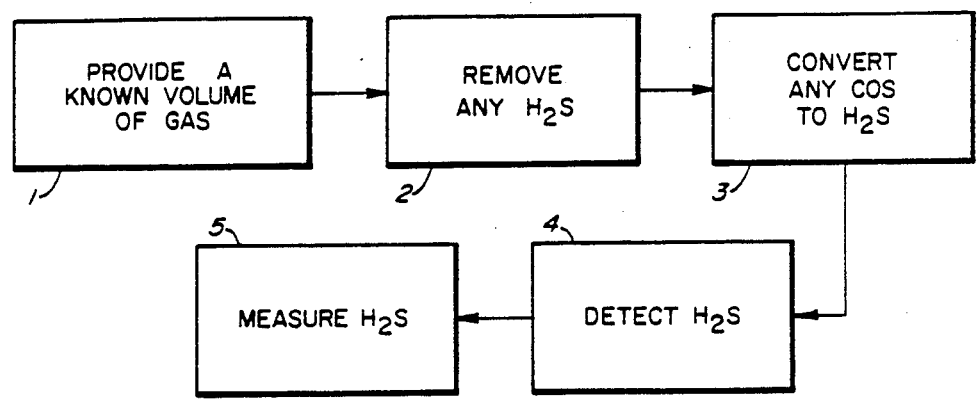
FIG. 1 shows a block diagram of the process steps of the invention.

Referring now to the block diagram of FIG. 1, there are shown the process steps of the invention. The first step in the process comprises providing a known volume of gas to be analyzed. This is indicated in block 1 of FIG. 1. A known volume of gas is necessary to determine the concentration of the carbonyl sulfide in the gas to be analyzed.

The next step shown in block 2 comprises removing any hydrogen sulfide ($H_2S$) from the known volume of gas. The presence of $H_2S$ in the gas prior to analysis would interfere with the carbonyl sulfide determination and, thus, must be removed. This can be accomplished in any convenient manner. Preferably the gas is brought into contact with one or more chemicals which will react with the $H_2S$ but which are substantially unreactive with the gas to be analyzed. The selection of such chemicals, then will depend upon the identity and characteristics of the gas being analyzed.

When carbon dioxide gas is being analyzed for the presence of carbonyl sulfide, the gas is preferably passed into contact with a lead acetate impregnated guard column. In place of the lead acetate, other chemicals can be used. Examples of such chemicals include but are not limited to cadmium chloride.

The chemical selected as well as its physical form are not critical as long as the chemical is of a type and form which will permit gas passage for intimate contact and will react with any $H_2S$ present without reacting with the gas being analyzed or add new contaminants. It will be apparent that the identity and characteristics of the gas being analyzed will dictate the best choice of a chemical to be employed.

Best results are obtained using the chemicals in some form which provides a large surface area of contact. As a practical matter, this is conveniently accomplished using beads or microspheres of a ceramic or other relatively non-reactive material onto which the active chemical is adhered. Alternatively, chemicals in liquid form can be employed through which the gas is bubbled in order to remove any $H_2S$.

After all of the $H_2S$ has been removed from the gas by contact with a chemical reactive with $H_2S$, any carbonyl sulfide present in the gas is then converted to $H_2S$ as indicated in block 3 of FIG. 1.

Again, the exact method for accomplishing this end will depend upon the identity and characteristics of the gas being analyzed. A preferred method which can be employed for many gases is to humidify the gas and then bring the humidified gas into contact with an hydrolysis catalyst. When this method is employed, it is necessary to humidify the gas to enable its subsequent hydrolysis. When in contact with the hydrolysis catalyst, the carbonyl sulfide reacts with water to produce hydrogen sulfide and carbon dioxide.

When $CO_2$ gas is being analyzed, it is preferably humidified by bubbling the $C_2$ gas through water acidified with sulfuric acid. Since carbon dioxide is somewhat soluble in water, it is necessary to use water which has been acidified, for example with sulfuric acid to humidify it. The presence of the acid in the water prevents the gas from dissolving therein. An advantage of using sulfuric acid to acidify the water is that it puts S− ions into the water. This effectively prevents any S− ions in the gas to be analyzed from dissolving in the water.

As an alternative, in the event that CO 2 gas is being analyzed, the water can be acidified by bubbling the $CO_2$ through the water until a pH in the range of 3–4 is reached. This results through the formation of $H_2CO_3$.

Preferably the water is acidified to a pH in the range of about pH 3 to about pH 4. Other acids can be used in place of the sulfuric acid, depending upon the identity and characteristics of the gas being analyzed. The acid used should not react with the gas or add contaminants to it.

Any convenient method can be used to humidify the gas. A preferred method comprises bubbling the gas through water. An alternative method would be to pass the gas through an atomized mist of water. However, it is not desired to cause the water mist to be entrained by the gas passing through it since large amounts of water are not required.

After the gas has been humidified, it is brought into contact with the hydrolysis catalyst. In the case of carbon dioxide, this catalyst is preferably an alumina (aluminum oxide) hydrolysis catalyst. Other catalysts which can be used include but are not limited to zinc oxide and platinum embedded in aluminum.

The hydrolysis catalyst is preferably in a form which will provide a large surface area for reaction. This is conveniently accomplished using beads or microspheres of a ceramic or other relatively non-reactive material onto which the active chemical is adhered. A column of the catalyst in a finely divided form is a preferred.

Also, the hydrolysis catalyst is preferably maintained at an elevated temperature in order to achieve the greatest efficiency. The exact temperature will depend upon the gas being analyzed. Preferably in the case of $CO_2$ a temperature in the range of about 350° F. to about 800° F. is preferred. Using an alumina hydrolysis catalyst and a temperature of 400° F. has produced excellent results with carbon dioxide gas.

When the humidified carbon dioxide is brought into contact with the hydrolysis catalyst, any carbonyl sulfide which is present in the carbon dioxide gas stream reacts in the presence of the catalyst with the water introduced by humidifying. The reaction causes the carbonyl sulfide to form hydrogen sulfide ($H_2S$) and carbon dioxide. This reaction is believed to take place in the manner shown below:

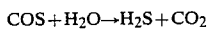

$$COS + H_2O \rightarrow H_2S + CO_2$$

The hydrogen sulfide produced through contact with the hydrolysis catalyst or by any other means is then detected as indicated in block 4 and measured as indicated in block 5 of FIG. 1.

This can be accomplished by standard means such as by passage through a hydrogen sulfide indicating color tube containing lead acetate. Here the hydrogen sulfide reacts with the lead acetate to produce lead sulfide and acetic acid which reaction is indicated by a quantifiable color change. This color tube can be the same kind of tube used in the step to initially remove any $H_2S$ present in the gas. Thus, other chemicals such as cadmium chloride could be used in place of lead acetate.

This is a very accurate indicator of the amount of carbonyl sulfide initially present in the gas since the hydrogen sulfide indicating color tube reacts to produce a quantifiable color change in the tube with respect to the amount of hydrogen sulfide contained in the gas. This value is directly related to the original amount of carbonyl sulfide contained in the original gas sample. Simply stated, each mole of hydrogen sulfide indicated represents one mole of carbonyl sulfide originally present in the gas being analyzed.

THE APPARATUS

Figure 2:
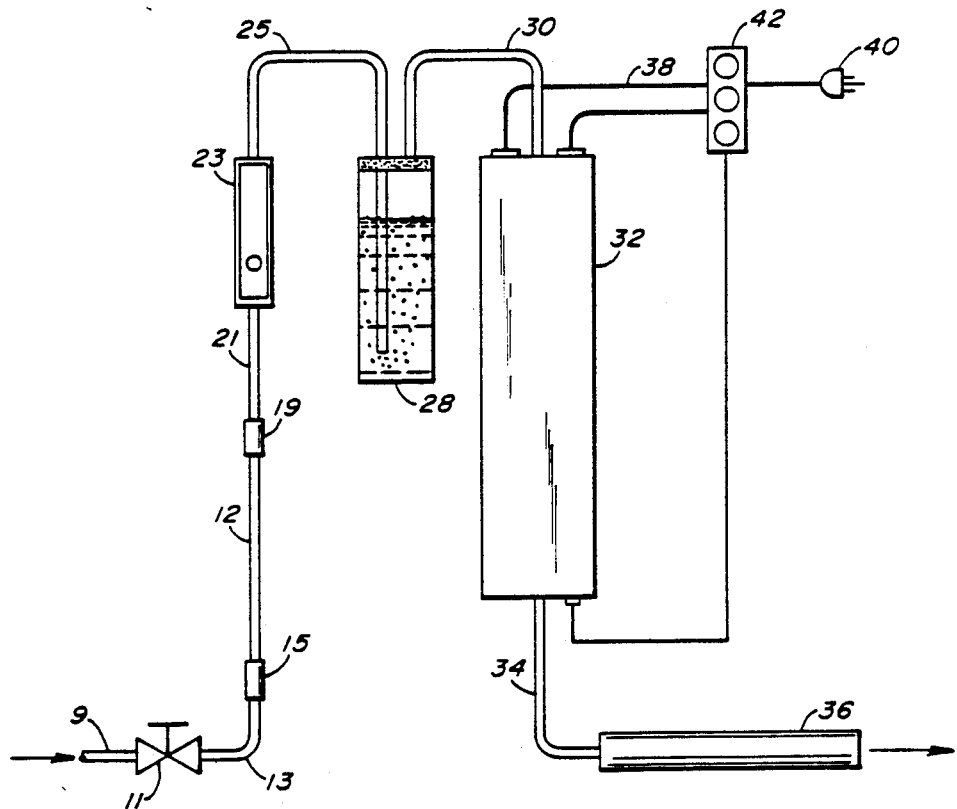
FIG. 2 shows a schematic representation of the portable analyzer of the invention.

Referring now to FIG. 2, there is shown a schematic representation of the analyzer of the invention. As shown, a gas inlet in the form of a conduit 9 which is shown partially broken away is connected to a needle valve 11 which controls gas flow to be tested. The valve 11 directs the gas first to a column 12 containing a chemical reactive with $H_2S$.

One end of column 12 communicates with the valve 11 by means of a conduit 13 and a connector 15 and the opposite end communicates with a flow meter 23 through connector 19 and conduit 21. The flow meter 23 discharges the gas stream through conduit 25 into a water bubbler 28 containing acidified water.

The water bubbler 28 communicates with a reaction block 32 containing an hydrolysis catalyst by means of conduit 30. The reaction block 32 connects with a hydrogen sulfide indicating color tube 36 containing a chemical reactive with $H_2S$ by means of a conduit 34. An electrical wire 38 with a plug 40 permits connection to an electrical power source not shown to provide power to the reaction block 32 in order to operate a heater not shown and heater and temperature controls 42.

In operation, a gas to be analyzed, for example, carbon dioxide, is passed through the needle valve 11. The needle valve 11 sets or controls the gas flow rate through the flow meter 23. This enables a determination of the gas volume analyzed. The gas volume is a function of the analysis time and the gas flow rate. A knowledge of the gas volume is needed to determine the concentration of the carbonyl sulfide in the gas being analyzed.

From the needle valve 11, the gas to be analyzed is passed through the column 12 which preferably comprises a lead acetate impregnated support guard column for hydrogen sulfide. This step removes any hydrogen sulfide present in the gas which would interfere with the carbonyl sulfide determination. In the support guard column 12, the lead acetate reacts with the hydrogen sulfide to form lead sulfide and acetic acid.

The gas exiting from the support guard column 12 which is now free of any hydrogen sulfide passes through the flow meter 23 where the gas flow rate is measured before entering the water bubbler 28.

The water bubbler 28 contains acidified water which acts to humidify the gas. The presence of the acid in the water prevents the gas from dissolving therein. It is necessary to humidify the gas to enable its subsequent hydrolysis in the reaction block 32.

The humidified gas exiting from the water bubbler 28 is introduced into the reaction block 32 which preferably contains a column of alumina (aluminum oxide) hydrolysis catalyst which is preferably maintained at a temperature of about 400 degrees F. This may be accomplished by any convenient means, but is conveniently accomplished with an electrical heater. Preferably, the reaction block 32 includes insulation surrounding the column of alumina or other hydrolysis catalyst. Also, the temperature is preferably determined and maintained by means of a temperature sensor/controller indicated at 42.

In the reaction block 32, any carbonyl sulfide which is present in the carbon dioxide gas stream reacts in the presence of the catalyst with the water introduced by passage through the bubbler. The reaction causes the carbonyl sulfide to form hydrogen sulfide ($H_2S$) and carbon dioxide.

The hydrogen sulfide produced in the reaction block 32 is then passed into the hydrogen sulfide indicating color tube 36, preferably containing lead acetate. Here the hydrogen sulfide reacts with the lead acetate to produce lead sulfide and acetic acid which reaction is indicated by a color change.

The amount of carbonyl sulfide initially present in the gas to be analyzed corresponds to the molar equivalent of hydrogen sulfide detected in the hydrogen sulfide indicating color tube.

Gas exiting the lead acetate color tube 36 can be vented to the atmosphere or to any desired area.

Connections between the various components of the analyzer are preferably made with "Tygon" tubing which is a trademark for a vinyl compound having anticorrosive properties. Other types of anticorrosive materials can also be used for the tubing.

All of the components of the dectector are relatively small in size and can be assembled in an enclosure about the size of a briefcase for portability and convenience.

The following example is provided to illustrate the invention and is not intended to constitute a limitation thereof.

EXAMPLE

Test mixtures of carbon dioxide gas containing from 0.3 ppm to 2.6 ppm COS were prepared. The mixtures were calibrated with a Tracor gas chromatograph using a flame photometric detector.

The test mixtures were then analyzed according to the invention process using the apparatus substantially as described.

Using flow rates from 200 to 300 ml/min, each of the test mixtures was passed first through the lead acetate guard column, then into the bubbler containing sulfuric acid to provide a pH of 3-4. The humidified gas exiting the bubbler was then passed through the reaction block which contained alumina and which was maintained at a temperature of 400° F.

The carbon dioxide exiting the reaction block was then passed through a Drager hydrogen sulfide detection color tube. The results are given in the table below:

| COS Concentration as measured by the Tracor FPD | COS Concentration as measured by the Invention Detector using a Drager Tube l/c | Variance | Percent of actual Detected |
|---|---|---|---|
| 0.291 ppm | 0.235 ppm | 0.00002 | 80.76% |
| 0.301 ppm | 0.251 ppm | 0.00002 | 83.39% |
| 0.71 ppm | 0.753 ppm | 0.0012 | 106.06% |
| 2.40 ppm | 2.075 ppm | 0.1118 | 86.40% |
| 2.61 ppm | 2.35 ppm | 0.0051 | 90.04% |

The Tracor standardization has an error of $-\pm 0.085$ ppm due to noise in the signal. The above results indicate that the detector is reliable over the above range. From the first observable stain up to a confirmatory reading at a half-tube stain reading the detection is quite linear. The differences between the actual readings measured by the Tracor FPD and that measured by the invention dectector are believed to result from adsorption of both $H_2O$ and COS in the reactor and/or the water bubbler.

The invention thus described provides a process and apparatus which is portable and which enables the on-site detection of low ppm concentrations of COS in gases, especially $CO_2$.

Various modifications of the invention are contemplated which will be obvious to those skilled in the art and which can be resorted to without departing from the spirit and scope of the invention as defined by the following appended claims.

I claim:

1. A process for the detection of carbonyl sulfide in a gas comprising:
    providing a known volume of gas to be analyzed;
    removing any $H_2S$ from said volume of gas;
    converting carbonyl sulfide present in said gas volume to $H_2S$;
    detecting and measuring the resulting $H_2S$ determining the amount of carbonyl sulfide present in the original gas volume by comparing the amount of $H_2S$ detected as a molar equivalent of said carbonyl sulfide present in the original gas volume.

2. A process for the detection of carbonyl sulfide in a gas as claimed in claim 1 wherein:
    any said $H_2S$ initially present is removed from said gas volume by passing said known volume of gas into contact with a chemical reactive with $H_2S$ but substantially unreactive with said gas to remove any $H_2S$ from said gas.

3. A process as claimed in claim 2 wherein said chemical is lead acetate.

4. A process for the detection of carbonyl sulfide in a gas as claimed in claim 1 wherein:
    said carbonyl sulfide in said gas volume is converted to $H_2S$ by passing said gas through an acidified water solution to humidify the gas followed by contacting said humidified gas with an hydrolysis catalyst at a temperature sufficiently high to cause carbonyl sulfide in the gas to react to form $H_2S$.

5. A process as claimed in claim 4 wherein said water solution is acidified to a pH in the range of about pH 3 to about pH 4.

6. A process as claimed in claim 4 wherein said hydrolysis catalyst is alumina and said water is acidified with sulfuric acid.

7. A process as claimed in claim 4 wherein said water is acidified by passage of $CO_2$ through said water until a pH in the range of about pH 3 to about pH 4 is reached.

8. A process as claimed in claim 1 wherein said $H_2S$ is detected by passage through a $H_2S$ indicating color tube.

9. A process as claimed in claim 1 wherein said $H_2S$ indicating color tube contains lead acetate.

10. A process for the detection of carbonyl sulfide in a gas as claimed in claim 1 wherein:
    said known volume of gas is provided by controlling the gas flow rate through a flowmeter and determining the volume by measuring the time of flow.

11. A process for the detection of carbonyl sulfide in a gas as claimed in claim 1 wherein:
said gas is $CO_2$.

12. A process for the detection of carbonyl sulfide in $CO_2$ comprising:
providing a known volume of $CO_2$ gas;
passing said known volume of $CO_2$ gas into contact with a chemical reactive with $H_2S$ but substantially unreactive with said $CO_2$ gas to remove any $H_2S$ from said $CO_2$ gas;
passing said $CO_2$ gas through an acidified water solution to humidify said $CO_2$ gas:
contacting said humidified $CO_2$ gas with an hydrolysis catalyst at a temperature sufficiently high to cause carbonyl sulfide and $H_2O$ vapor in the gas to react to form one mole of $H_2S$ for each mole of carbonyl sulfide; and,
passing said $CO_2$ gas through a $H_2S$ detecting color tube to detect the amount of $H_2S$ present in the $CO_2$ gas, and determining the amount of carbonyl sulfide present in the original $CO_2$ gas volume by comparing the amount of $H_2S$ detected as a molar equivalent of said carbonyl sulfide present in the original $CO_2$ gas volume.

13. A process for the detection of carbonyl sulfide in $CO_2$ as claimed in claim 12 wherein:
said chemical reactive with $H_2S$ is lead acetate, and said $H_2S$ indicating color tube contains lead acetate.

14. A process for the detection of carbonyl sulfide in $CO_2$ as claimed in claim 12 wherein:
said acidified water solution comprises sulfuric acid and water and has a pH in the range of about pH 3 to about pH 4.

15. A process for the detection of carbonyl sulfide in $CO_2$ as claimed in claim 12 wherein:
said temperature of said contact with the aluminum oxide hydrolysis catalyst is in the range of about 35° F. to about 800° F.

16. A process for the detection of carbonyl sulfide in $CO_2$ as claimed in claim 12 wherein said known volume of gas is provided by controlling the gas flow rate through a flowmeter and determining the volume by measuring the time of flow.

* * * * *